United States Patent [19]
Della Valle et al.

[11] Patent Number: 5,814,650
[45] Date of Patent: Sep. 29, 1998

[54] BIOTIN AMIDES ABLE TO CONTROL GLUCIDIC METABOLISMS UNDER DYSMETABOLIC CONDITIONS AND RELATIVE THERAPEUTICAL COMPOSITIONS

[75] Inventors: Francesco Della Valle; Silvana Lorenzi, both of Padova; Gabriele Marcolongo, Carrara San Giorgio; Lauro Galzigna, Padova, all of Italy

[73] Assignee: Lifegroup S.p.A., Rome, Italy

[21] Appl. No.: 825,458

[22] Filed: Mar. 28, 1997

Related U.S. Application Data

[63] Continuation of Ser. No. 280,321, Jul. 25, 1994, abandoned, which is a continuation-in-part of Ser. No. 127,339, Sep. 28, 1993, abandoned.

[30] Foreign Application Priority Data

Sep. 28, 1992 [IT] Italy .............................. MI92A2232 U

[51] Int. Cl.$^6$ ................................................. A61K 31/415
[52] U.S. Cl. .................... 514/387; 548/303.7; 548/304.1
[58] Field of Search ............................. 548/303.7, 304.1; 514/387

[56] References Cited

U.S. PATENT DOCUMENTS

| | | | |
|---|---|---|---|
| 2,519,530 | 8/1950 | Wolf et al. .............................. | 260/309 |
| 4,054,740 | 10/1977 | Field ...................................... | 548/303 |
| 4,709,037 | 11/1987 | Sigler ..................................... | 546/271 |
| 4,908,453 | 3/1990 | Cocuzza ................................. | 548/113 |

FOREIGN PATENT DOCUMENTS

| | | |
|---|---|---|
| 3629194 | 3/1987 | Germany . |
| 8907097 | 8/1989 | WIPO . |

OTHER PUBLICATIONS

Green, N.M.; Konieczny, L.; Toms, E.J. and Valentine, R.C. Biochem. J. (1971) vol. 125, pp. 781–791.
Jasbir Chauhan and Krishnamurti Dakshinamurti, Transcription Regulation of the Glucokinase Gene by Biotin in Starved Rats, The Journal of Biological Chemistry, vol. 266, No. 16, Jun. 1991, pp. 10035–10038.
John C. Coggeshall et al, Biotin Status and Plasma Glucose in Diabetics, N.Y. Acad. Sci. 447, 1985, pp. 389–392.
A. Reddi et al, Biotin Supplementation Improves Glucose and Insulin Tolerances in Genetically Diabetic KK Mice, Life Sciences, vol. 42, 1988, pp. 1323–1330.
Roth, Karl S., Biotin in Clinical Medicine—A Review, The American Journal of Clinical Nutrition 34: Sep. 1981, pp. 1967–1974.
Krishnamurti Dakshinamurti and Jasbir Chauhan, Biotin, Vitamins and Hormones, vol. 45, 1989, pp. 337–385.
K. Dakshinamurti and C. Cheah–Tan, Biotin–Mediated Synthesis of Hepatic Glucokinase in the Rat, Archives of Biochemistry and Biophysics 127, 1968, pp. 17–21.
D. Koutsikos et al, Biotin for Diabetic Peripheral Neuropathy, Biomed & Pharmacother, 1990, 44, pp. 511–514.
Thomas Kempe et al, Chemical and Enzymatic Biotin–Labeling of Oligodeoxyribo–nucleotides, Nucleic Acids Research, vol. 13, No. 1, 1985, pp. 45–57.
Marlon M. Bradford, A Rapid and Sensitive Method for the Quantitation of Microgram Quantities of Protein Utilizing the Principle of Protein–Dye Binding, Analytical Biochemistry 72, 1976, pp. 248–254.
Hanssen et al, "Diabetic Control and Microvascular Complications: The Near–Normoglycaemic Experience", Diabetologia 29: 677–684 (1986).
Chapter 34 in "Remington's Pharmaceutical Sciences" (The Philadelphia College of Pharmacy and Science, 1990) pp. 682–683.
Shami et al, "Microangiopathy in Diabetes Mellitus: II Features, Complications and Investigation", Diabetes Research, 17, 157–158 (1991) pp. 157–168.
Chapter 2.20 in Vogel's Textbook of Practical Organic Chemistry, Fifth Ed., Longman Group UK, 1989) pp. 135–136.
"Peripheral Neuropathies", World Health Organization (WHO), Technical Report Series 654 (1980), pp. 88–93.
Krishnamurti Dakshinamurti et al, "Biotin" in Vitamins and Hormones Advances in Research and Applications, vol. 45, Ed. by Aurbach and McCormick, Academic Press, Inc. (1989), pp. 337–384.
Patent Abstracts of Japan, vol. 4, No. 85 (C–015) 18 Jun. 1980 & JP–A–55 050 863 (Sumitomo Chem. Co., Ltd.) 14 Apr. 1980.
Patent Abstracts of Japan, vol. 16, No. 470 (C–0990) 30 Sep. 1992 & JP–A–04 169 528 (tanabe seiyaku co. ltd.) 17 Jun. 1992.
Heiko J. Luhmann and Uwe Heinemann, Journal of Neurophysiology, Apr. 1992, vol. 67, No. 4, pp. 798–811.
Green et al, Biochem J., (1971), vol. 123 pp. 781–791.

Primary Examiner—Johann Richter
Assistant Examiner—Laura L. Stockton
Attorney, Agent, or Firm—Stevens, Davis, Miller & Mosher, L.L.P.

[57] ABSTRACT

Described herein are biotin amides which are able to control glucidic metabolism under dysmetabolic conditions and relative therapeutical compositions for the treatment of insulin-independent diabetes, insulin-dependent diabetes and relative complicating diseases, such as peripheral neuropathies and other associated chronic invalidating disorders.

15 Claims, No Drawings

BIOTIN AMIDES ABLE TO CONTROL GLUCIDIC METABOLISMS UNDER DYSMETABOLIC CONDITIONS AND RELATIVE THERAPEUTICAL COMPOSITIONS

RELATED U.S. APPLICATIONS

This application is a Continuation of application Ser. No. 08/280,321, filed Jul. 25, 1994 now abandoned, which is a continuation-in-part of application Ser. No. 08/127,339, filed Sep. 28, 1993 now abandoned.

FIELD OF THE INVENTION

The present invention refers to the use of biotin amides in the therapeutic treatment of diabetes and its complicating diseases and to pharmaceutical compositions comprising said amides.

PRIOR ART DISCLOSURE

The clinical role of biotin, better known as vitamin H, was determined in 1942 by Sidenstricker and coworkers, who demonstrated that the so called "egg white injury" could be eradicated by administering biotin.

Before, other researchers had indeed identified this syndrome in animals subjected to a diet consisting only of egg white, and it could be prevented by biotin administration.

Sidenstricker's experiment was directed to demonstrate which were the consequences caused by vitamin H deficiency in human organism.

In fact in patients subjected to a diet of egg white, in which biotin results to be linked to a protein, avidin, not rendering bioavailable vitamin H, a biotin deficit state was observed.

As it clearly resulted from this experiment and from the following ones, this deficit was associated with clinical phenomena which, depending on the seriousness and on the symptoms, ranged from non pruriginous dermatitis to maculosquamous dermatitis and other disorders, such as mental state alterations, myalgia, hyperesthesia, localized paresthesia, anorexia and coronary ischemia.

All these secondary phenomena disappeared and the patients returned to normality after a prolonged biotin administration for a determined period of time.

In the same years also the biologic role of biotin was found: Vitamin H acts as a co-factor in carboxylation enzymatic reactions. In this connection, in the last 20 years, importance has been ascribed in applying enzymatic reactions co-factors for the therapy of human diseases.

Successively it was demonstrated that biotin, because of its peculiarity as a cofactor in enzymatic reactions, could be advantageously used in therapy in the same way as pyridoxine and vitamin D.

For example it was found that, whereas biotin proved uneffective for the treatment of diseases caused by single carboxylase enzymes insufficiencies, such as the propionyl-CoA carboxylase deficit (which is the cause of ketotic hyperglycinemia), pyruvate-carboxylase deficit (which is the cause of lactic acidosis persisting during the various childhood phases), β-methyl-crotonylcarboxylase deficit (which may also cause in childish age spinal and muscular atrophy or again in childish age also a serious dysmetabolic acidosis), on the contrary biotin resulted effective for the treatment of diseases caused by multiple carboxylase enzymes deficiencies, whose symptoms are more or less common to those of the above mentioned pathologies and caused by single carboxylase enzymes deficiencies (K. S. Roth "Biotin in clinical medicine—a review", "The American Journal of clinical nutrition", 1981, 34, 1967–1974).

Besides, Vitamin H proved particularly effective in the treatment of newborn seborrheal dermatitis, whose cause has not yet been well ascertained, but seeming to be ascribable to low content of vitamin H in mother's milk, defective digestion or persistent diarrhea (Krishnamurti Dakshinamurti and Jasbir Chauan, Biotin-Vitamins and Hormones, 1989, 45, 337–385).

The evidences concerning a possible involvement of biotin in conditions of glucose altered metabolism began in 1968, when the ability of biotin to restore the activity of a key glycolytic enzyme, glucokinase, was demonstrated (Dakshinamurti K., Cheah-Tan C., Arch.Biochem. & Biophys., 1968, 127, 17–21). This substance is in fact the catalyst of the initial step of the glucose utilization by the cell, therefore it is the enzyme mostly involved in the control of glucose hepatic uptake.

It is in fact known that glucokinase enzyme regulates hematic glucose, namely glycemia, contemporaneously controlling the utilization and storing of hepatic glucose in the form of glycogen, and in pancreas islets glucokinase is considered to act as a glucose sensor, regulating insulin production.

The effect of biotin on hepatic glucokinase resulted to be dependent from the genic regulation of this enzyme and mediated by mRNA induction for the same enzyme, therefore an analogous behaviour to that of insulin (Chauan J. et al., J. Biol. Chem., 1991, 266, 10025–10038).

In addition biotin, thanks to its co-factor role, may have an important function in the control of the hematic glucose, also controlling another enzymatic route.

Biotin is in fact able to activate as a co-factor in carboxylation reactions besides glucokinase, also pyruvate-carboxylase, namely the enzyme involved in gluconeogenesis; this activity is only apparently in contrast with glucose utilization activity stimulated by glucokinase activation, since, indeed, pyruvate carboxylase is a key enzyme in the activation of Krebs cycle, an activation determining the use of hematic glucose for fatty acids synthesis. Also acting on pyruvate carboxylase biotin can therefore cause a reduction of glycemia.

These considerations were also supported by clinical evidences correlating biotin levels to glycemia under diabetes mellitus conditions. It was in fact observed that hyperglycemia typical of diabetes mellitus was correlated to an increase of biotin in the tissue levels, since to this increase a glucose increase corresponded.

In addition it was observed that the same diabetic patients, once the insulin treatment was interrupted, the use of placebo caused a high increase of plasmatic glucose, whereas the use of biotin (16 mg/die for 1 week) induced a significant reduction in the hematic glucose levels (Coggeshall J. C. et al., NY Acad.Sci., 1985, 447, 389–392).

Also in diabetes experimental models, as in the genetically KK diabetic mice being moderately hyperglycemic and insulin resistant diabetic non biotin deficient, high biotin doses resulted effective. In particular, the treatment with biotin (2 mg/kg for 14 days) improved sensibly glucose tolerance of these animals (Reddi A. et al., Life Sciences, 1988, 42, 1323–1330).

More recently a very interesting evidence from the clinical point of view was issued, concerning the use of biotin not only for glucose metabolism normalization, but also for the treatment of neuropathy, a complicating disease very frequently associated with diabetes (Koutsikos D. et al., Biomed & Pharmacother., 1990, 44, 511–514).

In fact the intramuscular treatment with biotin for 6 weeks, associated with the oral administration of the same active principle at a daily dose of 5 mg for about 2 years, produced a marked improvement in the subjective neurologic symptoms (muscular cramps and paresthesiae, improvement in walking and in climbing stairs, disappearance of restless leg syndrome) as well as a slight improvement in conduction velocity at the level of the motor nerves and of the action sensory potentials.

The decrease in pyruvate-carboxylase activity consequent to the decrease in biotin levels, according to the same authors, should be the cause of neuropathic phenomena connected with diabetes, as well as of neuropathic symptomatologies associated with other dysmetabolic and toxic conditions, such as alcoholism and uremia. Though the above described important results, concerning the activity of biotin in models which can be correlated to diabetes and in the same diabetes, suggest a wide use of biotin, alone or in association with antidiabetic drugs orally administered for the treatment of insulin-independent diabetes, or in association with insulin in case of insulin-dependent diabetes, no therapeutic use of this important vitamin has been developed up to today.

This is probably caused by its quick and non persistent action, rendering difficult the definition of a therapeutical and posological scheme.

On the other hand, it is generally accepted that through a diet it is possible to have a sufficient biotin supply to cover physiological needs. In fact biotin is present in many and widely diffused aliments (milk, egg yolk etc.), and it is also produced by intestinal flora.

If this is true under normal conditions, it is however to be considered that in diabetic patients important alterations in the plasmatic levels of biotin have been observed and that only free biotin seems to regulate the use of hematic glucose.

In view of the foregoing, it results particularly interesting, from a therapeutical point of view, to have biotin derivatives able to act as the same vitamin, possibly maintaining at the same time the highest hematic levels. It must be finally considered that biotin is poorly soluble in water and this property limits its use by general parenteral route, said use being very important under serious diabetic states or in some diabetic extremely complicating diseases, such as peripheral neuropathies and other associated chronic invalidating pathologies.

Under these conditions it can be of particular therapeutic utility to obtain a quick bioavailability of this vitamin administered alone or in association with oral hypoglycemic drugs in case of insulin-independent diabetes, or with insulin in case of insulin-dependent diabetes.

Therefore the need was felt to have water soluble biotin derivatives, allowing the use of this active principle not only by oral, but also by parenteral and in particular by intramuscular and intravenous route.

SUMMARY OF THE INVENTION

The Applicant has now unexpectedly found that amide derivatives of α or β biotin having general formula (I):

W—CONH—R—X     (I)

wherein
W is

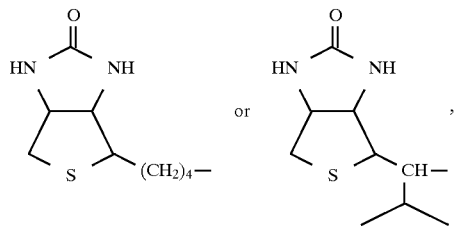

R is a bivalent radical of from 1 to 20 carbon atoms, having the meanings defined in one of the following classes:
A) a linear or branched alkylene radical, optionally substituted in the alkylene chain with at least one substituent selected from the group consisting of:

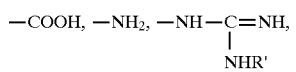

—H, —SH, —CO—, —OH and wherein R' is methyl or —H;
B) a cycloalkylene of from 3 to 7 carbon atoms;
C) an arylene or an arylalkylene radical optionally substituted on the aromatic ring with at least one —NO$_2$ group;

and X is selected from the group consisting of —H, —OH, —COOH,

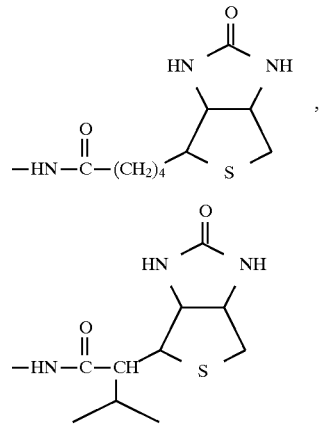

are able to act as hyperglycemia inhibitors, as well as to activate hepatic glucokinase in a higher degree than biotin as such. Another class of biotin amides, showing the activities described hereunder according to the present invention, is the following:

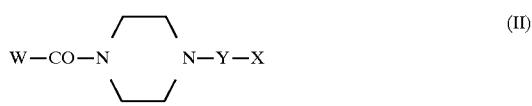

wherein W and X have the above mentioned meanings and Y is an alkylene radical.

Therefore the present invention relates to the use of the amides of general formula (I) and (II) in the therapeutic treatment of insulin independent diabetes, alone or optionally in association with antidiabetic drugs to be orally administered, in the treatment of insulin dependent diabetes, optionally in association with insulin, and in the treatment or prevention of diabetic complicating diseases, such as peripheral neuropathies.

The present invention relates also to therapeutical compositions for the treatment of insulin-independent diabetes, when optionally associated with hypoglycemic compositions orally administrable, insulin-dependent diabetes, when optionally associated with injectable therapeutic compositions containing as the active principle insulin, and diabetic complicating diseases, comprising an effective amount of amides of formula (I) or (II) in combination with suitable excipients and/or diluents.

DETAILED DESCRIPTION OF THE INVENTION

During the course of the instant description, in the compounds of formula (I) and (II) defined as β-derivatives of biotin the substituent W is

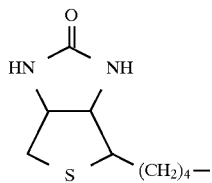

whereas in those defined as α-derivatives of biotin the substituent W is

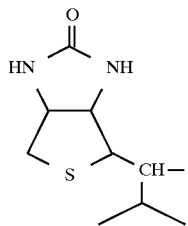

In the compounds of formula (I), the preferred meanings for R, when it is defined as in class A, are:

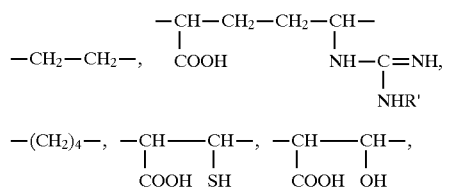

wherein R' is methyl or —H.

In the same compounds, when R is defined as in class B, it is preferably cyclohexylene;

in case R has the meanings given in class C, it is preferably selected from

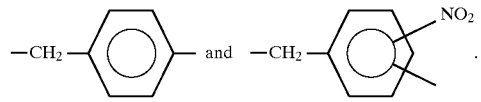

Particularly preferred compounds comprised in the general formula (I), which can be advantageously used in the therapeutical compositions according to the present inventions, are the following:

N-β-biotinyl-ethanolamine, namely the compound of formula (I) having R=—(CH$_2$)$_2$—, X=OH;

N-β-biotinyl-N$^G$-methyl-L-arginine, namely the compound of formula (I) having

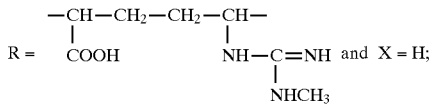

N-β-biotinyl-benzylamine, namely the compound of formula (I) having

N-β-biotinyl-4-amino-butanol, namely the compound of formula (I) having R=—(CH$_2$)$_4$—, and X=OH;

N,N'bis-(β-biotinyl)-ethylenediamine, namely the compound of formula (I) having

R = —(CH$_2$)$_2$— and

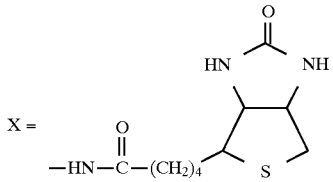

N-β-biotinyl-L-serine, namely the compound of formula (I) having

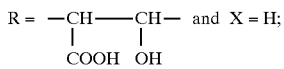

N-β-biotinyl-1-aminobutane, namely the compound of formula (I) having R=—(CH$_2$)$_4$—, and X=H;

N-β-biotinyl-aminocyclohexane, namely the compound of formula (I) having R=cyclohexylene, and X=H;

N-β-biotinyl-4-nitrobenzylamine, namely the compound of formula (I) having

N-β-biotinyl-L-arginine, namely the compound of formula (I) having

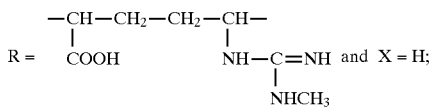

N-β-biotinyl-L-cysteine, namely the compound of formula (I) having

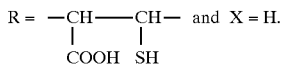

A preferred compound comprised in the formula (II) which can be advantageously used in the therapeutical compositions according to the present invention is N-β-biotinyl-N⁴-(2-hydroxyethyl)-piperazine, wherein Y is —CH₂—CH₂— and X is OH.

The amides of formula (I) and (II) according to the present invention are in particular able to control glucidic metabolism under dysmetabolic conditions, which can be correlated to the diabetic state and as such they can be used for insulin-independent diabetes therapy alone or optionally in association with antidiabetic drugs to be orally administered, and in insulin-dependent diabetes, optionally in association with insulin.

The derivatives of formula (I) and (II) can be also advantageously used for the treatment of diabetes complicating diseases, as for example peripheral neuropathies.

The use of the derivatives of formula (I) and (II) alone or in association with other antidiabetic drugs (insulin or oral hypoglycemic drugs) has to be established on the base of the diabetes type and the disorder severity.

The use of the sole derivatives of general formula (I) or (II) is preferable under weak hyperglycemia conditions, due for example to aging, whereas the combined use of the compound of formula (I) or (II) and other antidiabetic drugs is advisable in case of clear and serious diabetic state, or in case of diabetes on genetic base.

In these cases the association may have the advantage of a control on glycemia, using lower dosages of conventionally used antidiabetic drugs, inclusive insulin, than the usual posology. The compounds of formula (I) and (II) are preferably administered at dosages of from 5 to 40 mg/die and the therapeutic regimen is of chronic type or at repeated cycles.

In any case the posology has to be established on the base of medical criteria, as for example disorder severity, the presence of accompanying pathologies, patient's weight and age and the administration type.

The therapeutical compositions of the present invention may be generally administered by oral or parenteral route, preferably selected from subcutaneous and intramuscular route.

These compositions contain further to the active principle also pharmaceutically acceptable excipients or diluents.

The therapeutical compositions according to the present invention suitable to be parenterally administered are preferably in the form of aqueous and isotonic solution, whereas those suitable for the oral administration are in the form of lyophilized and granulated powders, tablets, dragees or capsules.

The amide derivatives of general formula (I) and (II) may be prepared according to two different processes.

The first process comprises the following steps:

a) treating α- or β-biotin, of formula W—COOH, in a polar aprotic solvent in the presence of a tertiary amine at a temperature lower than 0° C. with alkylchloroformate (III):

Cl—COOR''        (III)

wherein R'' is a C₁–C₁₀ alkyl, thereby obtaining the corresponding mixed anhydride of formula (IV);

W—COO—COOR''     (IV)

b) treating directly the reaction mixture containing the mixed anhydride (IV) with the amine of formula (V):

₂HN—R—X          (V)

thereby obtaining the corresponding amides of formula (I); or with the amine of formula (VI):

wherein R, Y and X have the above mentioned meanings, thereby obtaining the corresponding amides of formula (II).

The second process consists in reacting the α- or β-biotin ester of N-hydroxy-succinimide, in dimethylformamide at a temperature comprised between −10° C. and 0° C., with the above mentioned amine of formula (V) or (VI).

In both processes above cited, the polar aprotic solvent is preferably dimethylformamide or tetrahydrofuran.

Triethylamine, tributylamine and N-methyl-morpholine are preferably used as tertiary amine in both process.

In the first process, as the chloroformate isobutylchloroformate is preferably utilized, the temperature of step (a) is preferably comprised between −10° C. and 0° C., and the temperature of step (b) is preferably 0° C.

The products obtained with the processes of the present invention are preferably separated from the reaction mixture with conventional techniques, such as centrifugation, solvent evaporation, filtration, and are purified on anionic exchange resin, or by inverse phase chromatography, or by crystallization. The majority of the compounds of general formula (I) and (II) are soluble either in water or in organic solvents.

The following examples of preparation of the compounds of formula (I) and (II) of the present invention are reported for illustrative but not limitative purposes.

EXAMPLE 1

N-β-biotinyl-ethanolamine preparation 2.13 g triethylamine (21 mmoles) are added to 5.0 g of β-biotin (20.5 mmol) previously suspended in 80 ml of anhydrous tetrahydrofuran.

The suspension is then left at −10° C. under stirring. 2.87 g of isobutylchloroformate (21 mmol) are slowly added drop by drop in 30 min. under continuous stirring. The mixture is kept for 2 hours at −10° C., and subsequently for 15 hours at 0° C. 2.5 g of ethanolamine are then slowly added drop by drop in 30 min.

The mixture is brought to room temperature and left under stirring for 6 hours. The suspension is filtered on gooch G3 filter and the filtrate is discarded; the precipitate is solubilized in 100 ml of ethanol/water=1/1 and eluted on a column containing 50 ml anionic exchange resin (Amberlite IRA 400), generated under the acetate form. The eluate is concentrated under vacuum and the residue is crystallized from 70 ml of 80% ethanol. The product is then recovered by filtration, washed 3 times with 20 ml of cool ethanol and then dried under high vacuum.

Yield: 5.3 g

The physico-chemical characteristics of the derivative obtained by the process described in the Example 1 are:

| | |
|---|---|
| physical state | white crystalline powder |
| raw formula | $C_{12}H_{21}N_3O_3S$ |
| molecular weight | 287.32 |
| elemental analysis | C = 50.16%; H = 7.37%; N = 14.63%; O = 16.71%; S = 11.14% |
| solubility in organic solvents | >10 mg/ml in DMSO |
| solubility in water | >10 mg/ml |
| melting point | 172° C. |
| TLC | chloroform/methanol/water/28% NH₃ = 80/25/2/1; Rf = 0.40 |

EXAMPLE 2

N-β-biotinyl-N$^G$-methyl-L-arginine preparation 5.0 g β-biotin (20.5 mmol) are suspended in 80 ml of anhydrous DMF, to which 7.8 g (42 mmol) of tributylamine are added; the resulting suspension is stirred at −10° C. 2.87 g of isobutylchloroformate, corresponding to 21 mmol, are slowly added drop by drop in the space of 30 minutes, while maintaining the reaction mixture under continuous stirring.

The mixture is then left for 2 hours at −10° C., and successively for 15 hours at 0° C. 3.95 g of N$^G$-methyl-L-arginine are then slowly added; the mixture is stirred for 24 hours at 0° C., then at room temperature for further 6 hours. The solvent is evaporated from the reaction mixture under vacuum, the residue is diluted with water and purified by inverse phase chromatography, using a Lichrosorb RP18 resin column and, as the eluent, a mixture made of water/methanol=80/20. The eluate fractions containing the pure product are then collected and evaporated to dryness; the residue is solubilized in 50 ml of water and lyophilized.

Yield: 5.8 g.

The physico-chemical characteristics of the product N-β-biotinyl-N$^G$-methyl-L-arginine are the following:

| physical state | white amorphous powder |
|---|---|
| raw formula | $C_{17}H_{30}N_6O_4S$ |
| molecular weight | 414.53 |
| elemental analysis | C = 49.26%; H = 7.29%; N = 20.27%; |
| | O = 15.44%; S = 7.74% |
| solubility in organic solvents | >10 mg/ml in DMSO |
| solubility in water | >10 mg/ml |
| TLC | chloroform/methanol/water/28% NH$_3$ = 65/35/5/3; Rf = 0.22 |

EXAMPLE 2-A

N-β-biotinyl-N-$^G$-methyl-L-arginine preparation 7.0 g (20.5 mmol) of N-succinimidyl-β-biotinate are suspended in 80 ml of anhydrous DMF, to which 2.13 g of triethylamine are added, while maintaining the reaction mixture under continuous stirring at 0° C. 3.95 g of N$^G$-methyl-L-arginine are then added and the mixture is stirred for 2 hours at 0° C., then at 45° C. for further 4 hours. The desired product is then recovered and purified as described in Example 2.

Yield: 5.9 g.

EXAMPLE 3

N$^1$-β-biotinyl-N$^4$-(2-hydroxyethyl)-piperazine hydrochlorate preparation 5.0 g of β-biotin (20.5 mmol), are suspended in 80 ml of anhydrous THF, to which 2.13 g (21 mmol) of triethylamine are added; the resulting suspension is stirred at −10° C. 2.87 g (21 mmol) of isobutylchloroformate, are slowly added drop by drop in the space of 30 minutes, while maintaining the reaction mixture under continuous stirring. The mixture is left for 2 hours at −10° C. and successively for 15 hours at 0° C. 3.0 g of 1-(2-hydroxyethyl)piperazine are then slowly added drop by drop in the space of 30 minutes.

The mixture is then brought to room temperature and stirred for further 6 hours. The suspension thus obtained is then filtered and the filtrate is discarded; the solid precipitate is solubilized in 100 ml of water and titrated with diluted HCl until pH 4.0 is reached and the solution is concentrated under vacuum by using a rotavapor. The residue is purified by inverse phase chromatography, using a Lichrosorb RP18 resin column, and as the eluent a mixture made of water/ethanol=90/10. The eluate fractions containing the pure product are then collected and evaporated to dryness; the residue is dried under high vacuum.

Yield: 6.2 g.

The physico-chemical characteristics of the product N$^1$-β-biotinyl-N$^4$-(2-hydroxyethyl)-piperazine hydrochlorate are the following:

| physical state | white powder |
|---|---|
| raw formula | $C_{16}H_{28}N_4O_3S$ .HCl |
| molecular weight | 392.95 |
| elemental analysis | C = 48.91%; H = 7.44%; N = 14.26%; |
| | O = 12.22%; S = 8.16%; Cl = 9.02%; |
| solubility in organic solvents | >10 mg/ml in DMSO |
| solubility in water | >10 mg/ml |
| TLC | chloroform/methanol/water/28% NH$_3$ = 80/25/2/1; Rf = 0.50 |

EXAMPLE 4

N-β-biotinyl-benzylamine preparation 5.0 g (21 mmol) of β-biotin, are suspended in 80 ml of anhydrous THF, to which 2.13 g of triethylamine are added; the resulting suspension is stirred at −10° C. 2.87 g (21 mmol) of isobutylchloroformate, are slowly added drop by drop in the space of 30 minutes, while maintaining the reaction mixture under continuous stirring. The mixture is maintained for 2 hours at −10° C., and successively for 15 hours at 0° C. 3.5 g of benzylamine are then dropwise slowly added in the space of 30 minutes.

The mixture is then brought to room temperature and then left under stirring for further 6 hours. The solvent is then evaporated to dryness under vacuum and the obtained residue is crystallized from 120 ml of water. The product is then recovered by filtration, washed three times with 20 ml of cool water and finally dried under high vacuum.

Yield: 5.2 g

The physico-chemical characteristics of the product N-β-biotinyl-benzylamine are the following:

| physical state | white crystalline powder |
|---|---|
| raw formula | $C_{17}H_{23}N_3O_2S$ |
| molecular weight | 333.46 |
| elemental analysis | C = 61.23%; H = 6.95%; N = 12.60%; |
| | O = 9.60%; S = 9.62% |
| solubility in organic solvents | >10 mg/ml in DMSO; >10 mg/ml in ethanol. |
| solubility in water | poorly soluble |
| TLC | chloroform/methanol/water/28% NH$_3$ = 80/25/2/1; Rf = 0.69 |

EXAMPLE 5

N-β-biotinyl-4-amino-butanol preparation.

5.0 g of β-biotin (20.5 mmol) are suspended in 80 ml of anhydrous THF, to which 2.13 g (21 mmol) of triethylamine are added; the resulting suspension is stirred at −10° C. 2.87 g (21 mmol) of isobutylchloroformate are slowly added drop by drop in the space of 30 minutes, while maintaining the reaction mixture under continuous stirring. The mixture is left for 2 hours at −10° C. and successively for 15 hours at 0° C. 3.0 g of 4-amino-butanol are then slowly added drop by drop.

The mixture is then brought to room temperature for further 6 hours. The suspension thus obtained is then filtered and the filtrate is discarded. The residue is purified by inverse phase chromatography, using a Lichrosorb RP18 resin column, and as the eluent a mixture made of water/ ethanol=90/10. The eluate fractions containing the pure product are then collected and evaporated to dryness; the residue is dried under high vacuum.

Yield: 4.7 g.

The physico-chemical characteristics of the product N-β-biotinyl-4-amino-butanol are the following:

| physical state | white powder |
| --- | --- |
| raw formula | $C_{14}H_{25}N_3O_3S$ |
| molecular weight | 315.44 |
| elemental analysis | C = 53.31%; H = 7.99%; N = 13.32%; O = 15.22%; S = 10.17%; |
| solubility in organic solvents | >10 mg/ml in DMSO |
| solubility in water | >5 mg/ml |
| TLC | chloroform/methanol/water/28% $NH_3$ = 80/25/2/1; Rf = 0.45 |

EXAMPLE 6

N,N'bis-(β-biotinyl)-ethylendiamine preparation 5.0 g of β-biotin (20.5 mmol) are suspended in 80 ml of anhydrous DMF, to which 4.26 g (41 mmol) of triethylamine are added; the resulting suspension is stirred at −10° C. 2.87 g (21 mmol) of isobutylchloroformate, corresponding to 21 mmol, are slowly added drop by drop in the space of 30 minutes, while maintaining the reaction mixture under continuous stirring. The mixture is left for 2 hours at −10° C. and successively for 15 hours at 0° C. 0.6 g of ethylendiamine are then slowly added drop by drop.

The mixture is then brought to room temperature and stirred for further 20 hours. The suspension thus obtained is then filtered and the filtrate is discarded. The precipitate is washed three times with 10 ml of water and finally crystallized from a mixture made of water/ethanol=1/1. The product is recovered by filtration, washed three times with 20 ml of cool ethanol and finally dried under high vacuum.

Yield: 3.7 g.

The physico-chemical characteristics of the product N-N'-bis-(β-biotinyl)-ethylendiamine are the following:

| physical state | white crystalline powder |
| --- | --- |
| raw formula | $C_{22}H_{36}N_6O_4S_2$ |
| molecular weight | 512.70 |
| elemental analysis | C = 51.54%; H = 7.08%; N = 16.39%; O = 12.48%; S = 12.51%; |
| solubility in organic solvents | >2 mg/ml in hot DMSO |
| solubility in water | poorly soluble |
| TLC | chloroform/methanol/water/28% $NH_3$ = 80/25/2/1; Rf = 0.36 |

EXAMPLE 7

N-β-biotinyl-L-serine preparation 7.0 g (20.5 mmol) of N-succinimidyl-β-biotinate are suspended in 80 ml of anhydrous DMF, to which 2.13 g (21 mmol) of triethylamine are added, while maintaining the reaction mixture under continuous stirring at 0° C. 2.1 g of L-serine are then added and the mixture is stirred for 2 hours at 0° C., then at 45° C. for further 4 hours.

The solvent is evaporated under vacuum and the residue is diluted with cool water, to which 22 ml of HCl 1N are added: the formed precipitate is separated by filtration, and the filtrate solution is discarded. The precipitate is purified by inverse phase chromathography, using a Lichrosorb RP18 resin column, and as the eluent a mixture made of water/ethanol=70/30. The eluate fractions containing the pure product are then collected and evaporated to dryness; the residue is dried under high vacuum.

Yield: 5.1 g.

The physico-chemical characteristics of the product N-β-biotinyl-L-serine are the following:

| physical state | white powder |
| --- | --- |
| raw formula | $C_{13}H_{21}N_3O_5S$ |
| molecular weight | 331.40 |
| elemental analysis | C = 47.11%; H = 6.39%; N = 12.68%; O = 24.14%; S = 9.68%; |
| solubility in organic solvents | >10 mg/ml in DMSO |
| solubility in water | >10 mg/ml in 0.1M phosphate buffer at pH 7.4 |
| TLC | chloroform/methanol/water/28% $NH_3$ = 65/35/5/3; Rf = 0.28 |

EXAMPLE 7-A

N-β-biotinyl-L-serine preparation 5.0 g (20.5 mmol) of β-biotin are suspended in 80 ml of anhydrous DMF, to which 7.8 g (42 mmol) of tributylamine are added; the resulting suspension is stirred at −10° C. 2.87 g (21 mmol) of isobutylchloroformate, are slowly added drop by drop in the space of 30 minutes, while maintaining the reaction mixture under continuous stirring. The mixture is left for 2 hours at −10° C. and successively for 15 hours at 0° C. 2.1 g of L-serine are then slowly added drop by drop. The mixture is stirred for 24 hours at 0° C., then at room temperature for further 6 hours. The obtained product is then recovered and purified as described in example 7.

Yield: 5.2 g.

EXAMPLE 8

N-β-biotinyl-1-aminobutane preparation 5.0 g (20.5 mmol) of β-biotin are suspended in 80 ml of anhydrous THF, to which 2.13 g (21 mmol) of triethylamine are added; the resulting suspension is stirred at −10° C. 2.87 g of isobutylchloroformate (21 mmol) are slowly added drop by drop in the space of 30 minutes, while maintaining the reaction mixture under continuous stirring. The mixture is maintained for 2 hours at −10° C., and successively for 15 hours at 0° C. 2.0 g of 1-aminobutane are then slowly added drop by drop in the space of 30 minutes.

The mixture is then brought to room temperature and then left under stirring for further 6 hours. The solvent is then evaporated to dryness under vacuum and the obtained residue is crystallized from 250 ml of water. The product is then recovered by filtration, washed twice with 20 ml of distilled water and finally dried under high vacuum.

Yield: 4.25 g.

The physico-chemical characteristics of the product N-β-biotinyl-1-aminobutane are the following:

| physical state | white crystalline powder |
| --- | --- |
| raw formula | $C_{14}H_{25}N_3O_2S$ |
| molecular weight | 299.44 |
| elemental analysis | C = 56.16%; H = 8.42%; N = 14.03%; O = 10.69%; S = 10.71% |
| solubility in organic solvents | >10 mg/ml in DMSO. |
| solubility in water | poorly soluble |
| TLC | chloroform/methanol/water/28% $NH_3$ = 80/25/2/1; Rf = 0.66 |

EXAMPLE 9

N-β-biotinyl-aminocyclohexane preparation 7.0 g (20.5 mmol) of N-succinimidyl-β-biotinate are suspended in 80 ml of anhydrous DMF, to which 2.13 g (21 mmol) of triethylamine are added, while maintaining the reaction mixture under continuous stirring at 0° C. 2.0 g of cyclohexylamine are then added and the mixture is stirred for 2 hours at 0° C., then at room temperature for further 14 hours. The reaction mixture is then cooled to 0° C., then filtered; the filtered portion is then discarded, whereas the precipitate is washed three times with 20 ml of cool water and dried under high vacuum.

Yield: 4.57 g.

The physico-chemical characteristics of the product N-β-biotinyl-aminocyclohexane are the following:

| | |
|---|---|
| physical state | white powder |
| raw formula | $C_{16}H_{27}N_3O_2S$ |
| molecular weight | 325.48 |
| elemental analysis | C = 59.05%; H = 8.36%; N = 12.91%; O = 9.83%; S = 9.85% |
| solubility in organic solvents | >10 mg/ml in DMSO. |
| solubility in water | poorly soluble |
| TLC | chloroform/methanol/water/28% $NH_3$ = 80/25/2/1; Rf = 0.68 |

EXAMPLE 10

N-β-biotinyl-4-nitrobenzylamine preparation 5.0 g (20.5 mmol) of β-biotin are suspended in 80 ml of anhydrous THF, to which 2.13 g (21 mmol) of triethylamine are added; the resulting suspension is stirred at −10° C. 2.87 g (21 mmol) of isobutylchloroformate are slowly added drop by drop in the space of 30 minutes, while maintaining the reaction mixture under continuous stirring. The mixture is maintained for 2 hours at −10° C., and successively for 15 hours at 0° C. 3.77 g of 4-nitrobenzylamine hydrochlorate are then dissolved in 50 ml of cool water, to which 2 g of $K_2CO_3$ are added; the solution is extracted three times with 50 ml of ethyl acetate and the extracted portions are washed twice with 50 ml of cool water, collected and evaporated to dryness. The obtained residue is diluted with 10 ml of DMF and the obtained solution is slowly added drop by drop in the space of 30 minutes to the mixture previously prepared and maintained under continuous stirring at 0° C. The resulting mixture is then brought to room temperature and stirred for further 6 hours, then the solvent is evaporated to dryness under vacuum. The residue is then crystallized from 240 ml of water, the product is separated by filtration, washed three times with 20 ml of cool water and finally dried under high vacuum.

Yield: 5.47 g.

The physico-chemical characteristics of the product N-β-biotinyl-4-nitrobenzylamine are the following:

| | |
|---|---|
| physical state | yellowish crystalline powder |
| raw formula | $C_{17}H_{22}N_4O_4S$ |
| molecular weight | 378.46 |
| elemental analysis | C = 53.95%; H = 5.86%; N = 14.81%; O = 16.91%; S = 8.47% |
| solubility in organic solvents | >10 mg/ml in DMSO. |
| solubility in water | poorly soluble |
| TLC | chloroform/methanol/water/28% $NH_3$ = 80/25/2/1; Rf = 0.63 |

EXAMPLE 11

N-β-biotinyl-L-arginine preparation 7.0 g (20.5 mmol) of N-succinimidyl-β-biotinate are suspended in 80 ml of anhydrous DMF, to which 2.13 g (21 mmol) of triethylamine are added, while maintaining the reaction mixture under continuous stirring at 0° C. 3.83 g of L-arginine are then added and the mixture is stirred for 2 hours at 0° C., then at 45° C. for further 4 hours. The solvent is evaporated from the reaction mixture under vacuum, the residue is diluted with water and purified by inverse phase chromathography, using a Lichrosorb RP18 resin column and, as the eluent, a mixture made of water/ethanol=1/1. The eluate fractions containing the pure product are then collected and evaporated to dryness; the residue is solubilized in 50 ml of water and lyophilized.

Yield: 5.6 g.

The physico-chemical characteristics of the product N-β-biotinyl-L-arginine are the following:

| | |
|---|---|
| physical state | white amorphous powder |
| raw formula | $C_{16}H_{28}N_6O_4S$ |
| molecular weight | 400.51 |
| elemental analysis | C = 47.98%; H = 7.05%; N = 20.98%; O = 15.98%; S = 8.01% |
| solubility in organic solvents | >10 mg/ml in DMSO |
| solubility in water | >10 mg/ml |
| TLC | chloroform/methanol/water/28% $NH_3$ = 65/35/5/3; Rf = 0.12 |

EXAMPLE 12

N-β-biotinyl-L-cysteine preparation 7.0 g (20.5 mmol) of N-succinimidyl-β-biotinate are suspended in 80 ml of anhydrous DMF, to which 2.13 g (21 mmol) of triethylamine are added, while maintaining the reaction mixture under continuous stirring at 0° C. 2.42 g of L-cysteine are then added and the mixture is stirred for 2 hours at 0° C., then at 45° C. for further 4 hours.

The solvent is evaporated under vacuum and the residue is diluted with cool water, to which 22 ml of HCl 1N are added; the formed precipitate is separated by filtration, and the filtrate is discarded. The obtained precipitate is purified by operating repeated washes in aqueous suspension at 45° C., and it is finally dried under high vacuum.

Yield: 4.4 g.

The physico-chemical characteristics of the product N-β-biotinyl-L-cysteine are the following:

| | |
|---|---|
| physical state | white powder |
| raw formula | $C_{13}H_{21}N_3O_4S_2$ |
| molecular weight | 347.46 |
| elemental analysis | C = 44.94%; H = 6.09%; N = 12.09%; O = 18.42%; S = 18.46%; |
| solubility in organic solvents | >10 mg/ml in DMSO |
| solubility in water | >10 mg/ml in 0.1M phosphate buffer at pH 7.4 |
| TLC | chloroform/methanol/water/28% $NH_3$ = 65/35/5/3; Rf = 0.35 |

The derivatives according to the present invention are then tested in order to define their biologic activity in experimental conditions of hyperglycemia induced both by fasting and in streptozotocin-induced diabetes. Hepatic glucokinase activity is examined in the experimental condition of fasting. Glycemia, insulinemia and the levels of Aceto-Acetate (Ac.Ac.) are examined in the diabetes induced by streptozotocin.

Experimental diabetes induced by streptozotocin 10 male Wistar rats (200 g) are divided into 4 groups; the first group is composed by the controls and to the remaining groups streptozotocin (STZ) is injected by intraperitoneal route (80 mg/kg). The third group is furthermore treated with biotin by intraperitoneal route (3 mg/kg), and the fourth group with biotinyl ethanolamine (Ex.No.1) again by intraperitoneal route (3 mg/kg). The treatment is repeated for three days, then a blood sample is taken for analysis on the fifth day from the initial treatment.

| Treatment | Glycemia mmol/l | Insulinemia mU/l | AcAc nmol/l |
|---|---|---|---|
| Controls | 6.1 ± 1.1 | 11.3 ± 1.1 | 0 |
| STZ | 33.6 ± 2.4 | 7.81 ± 2.0 | 1.04 ± 0 |
| STZ + Biotin | 7.4 ± 0.9 | 25.1 ± 1.5 | 0 |
| STZ + Ex. No. 1 | 6.0 ± 0.5 | 23.5 ± 1.8 | 0 |

Glycemia is normalized by the treatment with biotin and more consistently by biotinylethanolamine, as shown in the above reported data; analogously on the insulinemia both the biotinylethanolamine and the biotin as such are active.

Ex vivo hepatic glucokinasic activity

EXPERIMENT A

This experiment is carried out according to the method described by Chauhan et al. publication (J. Biol. Chem. 1991, 266, 10035), where it is reported that the rat hepatic glucokinase, depressed by fasting, is reactivated by the biotin administration. 15 Wistar rats, weighing on average 250 g, are divided into three groups: the first one represents the control, the second one is treated by intraperitoneal route with biotin (3 mg/kg) and the third group with biotinylethanolamine (Ex.No.1) again by intraperitoneal route (3 mg/kg). After 24 hours of fasting, the rats are treated with the compounds and 6 hours after treatment are sacrificed by decapitation.

Livers are homogenized in 5 volumes 50 mM Tris at pH 7, 0.15M KCl, 5 mM EGTA, 4 mM $MgCl_2$, and 2 mM dithiothreitol and centrifugated at 100.000×g for 60 minutes. The surnatant, frozen to −80° C., is used for the analyses, after proteins determination according to Bradford method (Anal. Biochem. 72, 248, 1976).

Glucokinase is dosed by spectrophotometry according to Dakshinamurti K. et al. (Can. J. Biochem. 46, 75, 1968), with the following results:

| Treatment | Glucokinasic activity (U./min/protein mg) |
|---|---|
| Controls | 2.20 ± 0.90 (mean ± stan. deviation) |
| biotin | 3.96 ± 0.70 |
| Ex. No. 1 | 4.27 ± 0.45 |

The differences obtained are significant (t Student test; p=0.01) and demonstrate that, in these experimental conditions, after 6 hours, biotinylethanolamine is more active than biotin. Experiments carried out with a less time period between the administration of the compound and the sacrifice show less pronounced differences. This brings to suppose that biotinylethanolamine derivative has a retarded action.

EXPERIMENT B

Also this experiment, like the previous one, is carried out by following Chauhan et al. method (J. Biol. Chem., 1991, 266, 10035), but in a different strain of animals.

Sprague Dawley rats weighing on average 260 g, left without food for 24 hours, are divided into 15 groups: each one of 13 groups is respectively intraperitoneally treated with 2 mg/kg of one of the compounds of the present invention, hereinbelow reported in Table 1, or with the same dosage of biotin, all these substances being previously dissolved in physiological solutions. The obtained results are compared with those of the two groups corresponding to normal rats feeded ad libitum and with untreated rats left without food for 24 hours; all the animals had free access to water.

Three hours after the treatment the rats are sacrificed by cerebral displacement. Their livers are homogenized by Potter (8–9 strokes/800 rpm) in a volume 1:4 of 50 mM Tris at pH 7.4, 0.15M KCl, 5 mM EDTA, and 2 mM DTT. The homogenates are centrifugated at 100.000×g for 60 minutes. Their proteic concentration is determined according to the above mentioned Bradford method (Anal. Biochem. 72, 248, 1976).

Glucokinase activity is evaluated according to Dakshinamurti K. et al. (Can. J. Biochem. 46, 75, 1968), and expressed as arbitrary units/proteic concentration of the samples.

The obtained results confirm that in the fasted rats for 24 hours a reduction on glucokinase activity is observed (3.078±0.181 Arbitrary Units/mg proteins) if compared with the animal normally fed, and that biotin is able to restore at least partially this enzymatic activity (3.662±0.280 UA/mg proteins).

The compounds of the present invention proved to increase in a higher degree than biotin the above mentioned depressed activity ever since three hours from their administration, as it clearly results from the following Table 1.

TABLE 1

Effect of the compounds of the present invention on depressed glucokinase activity, previously depressed by fasting, calculated as percentage of enzymatic activation with respect to that of the untreated group left without food (control group).

| administered compound | Glucokinase activity increase (%) |
|---|---|
| Biotin | 19 |
| N-α-biotinyl-$N^4$-(2-hydroxyethyl)-piperazine | 28 |
| N-β-biotinyl-benzylamine | 28 |
| N-β-biotinyl-4-aminobutanol | 25 |
| N,N'-bis-(β-biotinyl)-ethylendiamine | 31 |
| N-β-biotinyl-L-serine | 33 |
| N-β-biotinyl-1-aminobutane | 25 |
| N-β-biotinyl-aminocyclohexane | 22 |
| N-β-biotinyl-4-nitrobenzylamine | 32 |
| N-β-biotinyl-L-arginine | 35 |
| N-β-biotinyl-$N^G$-methyl-L-arginine | 20 |
| N-β-biotinyl-L-cysteine | 34 |

In order to render evident the industrial applications of the present invention, some examples of pharmaceutical compositions are reported hereinbelow. These compositions are given for illustrative purposes and are not to be considered limitative for the realization of the invention.

EXAMPLE 1
water-soluble tablets

| | |
|---|---|
| Biotinylethanolamine | 6 mg |
| Glycocoll | 62 mg |
| Sodium carboxymethylstarch | 22 mg |
| Polyethyleneglycol 6000 | 14 mg |
| Starch | 1 mg |
| Polyvinyl pyrrolidone | 5 mg |

EXAMPLE 2
granule sachets

| | |
|---|---|
| Biotinylethanolamine | 6 mg |
| Glycocoll | 964 mg |
| Polyvinyl pyrrolidone | 5 mg |
| Polyethyleneglycol 6000 | 5 mg |
| Peach flavouring essence | 20 mg |

EXAMPLE 3
2 ml vials

| | |
|---|---|
| Biotinylethanolamine | 6 mg |
| Bibasic sodium phosphate.12H$_2$O | 6 mg |
| Monobasic sodium phosphate | 0.5 mg |
| Sodium Chloride | 12 mg |
| Bidistilled water q.s. to | 2 ml |

We claim:

1. A therapeutic composition in dosage unit form, comprising, per dosage unit, between 5 to 40 mg of an active principle for the treatment of insulin independent diabetes or dependent diabetes and for the treatment of diabetic peripheral neuropathies, comprising as the active principle at least one amide of α or β biotin of formula (I):

wherein

W is

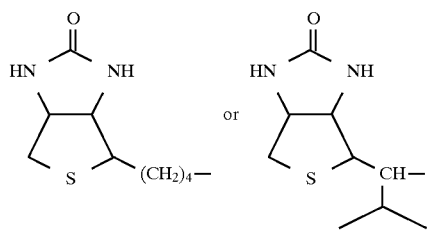

R is cyclohexylene, and

X is selected form the group consisting of —H, —OH, —COOH,

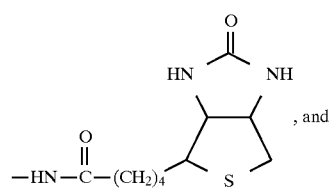

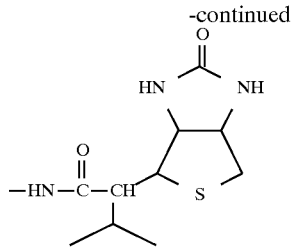

in combination with suitable excipients or diluents.

2. The therapeutic composition according to claim 1, wherein the compound of formula (I) is N-β-biotinyl-aminocyclohexane.

3. A therapeutic composition in dosage unit form, comprising, per dosage unit, between 5 to 40 mg of an active principle for the treatment of insulin independent diabetes or dependent diabetes and for the treatment of diabetic peripheral neuropathies, comprising as the active principle at least one amide of α or β biotin of formula (I):

wherein

W is

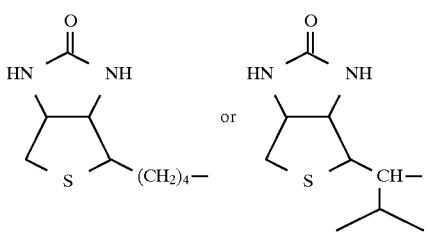

R is selected from the group consisting of

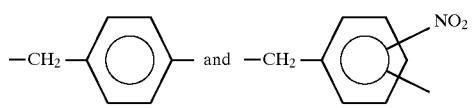

and X is selected form the group consisting of —H, —OH, —COOH,

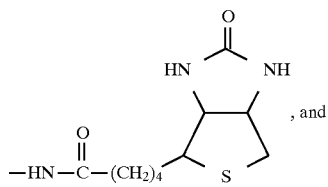

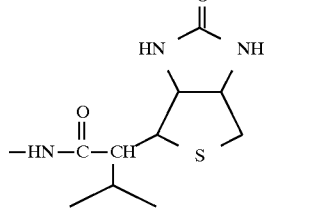

in combination with suitable excipients or diluents.

4. The therapeutic composition according to claim 3, wherein the compound of formula (I) is selected from the group consisting of N-β-biotinyl-benzylamine, and N-β-biotinyl-4-nitrobenzylamine.

5. A therapeutic method for the treatment of insulin independent diabetes or insulin dependent diabetes and for the treatment of diabetic peripheral neuropathies, comprising: administering a therapeutically effective amount of at least an amide of α or β biotin of formula (I):
wherein
W is

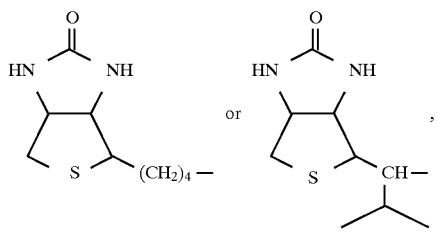

R is a bivalent radical of from 1 to 20 carbon atoms having the meanings defined in one of the following classes:
A) a linear or branched alkylene radical, optionally substituted in the alkylene chain with at least one substituent selected from the group consisting of:

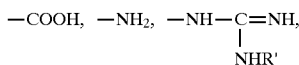

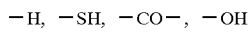

and wherein R' is methyl or —H;
B) a cycloalkylene of from 3 to 7 carbon atoms;
C) an arylene or an arylalkylene radical optionally substituted on the aromatic ring with at least one —NO₂ group;
and X is selected from the group consisting of —H, —OH, —COOH,

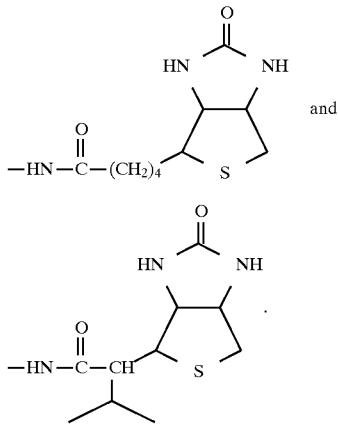

6. The therapeutic method according to claim 5, for the treatment of insulin in dependent diabetes wherein said amide of α or β biotin of formula (I) is administered together with hypoglycemic compositions orally administrable.

7. The therapeutic method according to claim 5, for the treatment of insulin dependent diabetes wherein said amide of α or β biotin of formula (I) is administered together with injectable therapeutic compositions, containing as the active principle insulin.

8. The therapeutic method according to claim 5, wherein said amide of α or β biotin of formula (I) is orally or parenterally administered.

9. The therapeutic method according to claim 5, wherein R in formula (I) is selected from the group consisting of:

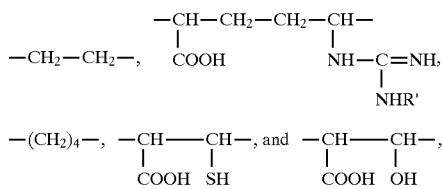

and R' has the above mentioned meanings.

10. The therapeutic method according to claim 5, wherein R in formula (I) is cyclohexylene.

11. The therapeutic method according to claim 5, wherein R in formula (I) is selected from the group consisting of:

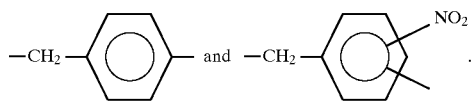

12. The therapeutic method according to claim 9, wherein the compound of formula (I) is selected from the group consisting of: N-β-biotinylethanolamine, N-β-biotinyl-N$^G$-methyl-L-arginine, N-β-biotinyl-4-amino-butanol, N,N'bis-(-β-biotinyl)-ethylenediamine, N-β-biotinyl-L-serine, N-β-biotinyl-1-aminobutane, N-β-biotinyl-L-arginine, and N-β-biotinyl-L-cysteine.

13. The therapeutic method according to claim 10, wherein the compound of formula (I) is N-β-biotinyl-aminocyclohexane.

14. The therapeutic method according to claim 11, wherein the compound of formula (I) is selected from the group consisting of N-β-biotinyl-benzylamine and N-β-biotinyl-4-nitrobenzylamine.

15. The method according to claim 12 wherein said compound of formula I is N-β-biotinylethanolamine.

* * * * *